(12) United States Patent
Mathies et al.

(10) Patent No.: US 6,913,679 B1
(45) Date of Patent: Jul. 5, 2005

(54) APPARATUS AND METHODS FOR HIGH RESOLUTION SEPARATION OF SAMPLE COMPONENTS ON MICROFABRICATED CHANNEL DEVICES

(75) Inventors: Richard A. Mathies, Moraga, CA (US); Brian Paegel, Berkeley, CA (US); Peter C. Simpson, Oakland, CA (US); Lester Hutt, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/249,274

(22) Filed: Feb. 11, 1999

(51) Int. Cl.[7] ................... G01N 27/447; G01N 27/453; G01N 30/02; B01L 3/02
(52) U.S. Cl. ...................... 204/451; 204/601; 422/70; 422/99
(58) Field of Search ................... 204/451, 601, 204/450, 600; 422/99, 100, 70, 129, 50, 81; 216/2; 210/656

(56) References Cited

U.S. PATENT DOCUMENTS

| 4,551,251 A | 11/1985 | Kolobow et al. | ............ 210/635 |
| 4,868,129 A | 9/1989 | Gibbons et al. | ............ 436/179 |

(Continued)

FOREIGN PATENT DOCUMENTS

| AU | WO99/24828 | | 5/1999 | ......... G01N/27/447 |
| EP | 0386925 A1 | * | 9/1990 | ......... G01N/27/447 |
| GB | 2128099 A | * | 4/1984 | ........... B01D/15/08 |
| WO | WO 96 04547 | | 2/1996 | |
| WO | 9822811 | * | 5/1998 | |
| WO | WO 9924828 | | 5/1999 | |

OTHER PUBLICATIONS

Koo et al. "Liquid flow in microchannels: experimental observations and computational analyses of microfluidics effects," J. Micromech. Microeng. 13 (2003) 568–579.*

C. Alexay et al., "Fluorescence scanner employing a Macro Scanning Objective," *SPIE* vol. 2705, 4/1996, pp. 63–72, month unknown.

(Continued)

*Primary Examiner*—Alex Noguerola
(74) *Attorney, Agent, or Firm*—Beyer Weaver & Thomas, LLP.

(57) ABSTRACT

Sample component separation apparatus and methods are described. An exemplary sample component separation apparatus includes a separation channel having a turn portion configured to reduce band-broadening caused by passage of a sample through the turn portion. To reduce band broadening caused by passage of a sample through a turn portion, the turn portion may be constructed and arranged to have a sample transport characteristic that is different from the corresponding sample transport characteristic of a substantially straight portion of the separation channel. For example, the turn portion may be configured with an effective channel width that is smaller than the effective channel widths of the substantially straight portion of the separation channel. The actual channel width of the turn portion may be smaller than the channel widths of the substantially straight portion; the effective channel width of the turn portion may be reduced by placing one or more sample transport barriers or constrictions in the turn portion of the channel. Alternatively, the sample velocity through the turn portion may be controlled so as to reduce band broadening. For example, sample transport barriers may be disposed in the turn portion so that sample components of a given band travel through the turn portion at substantially the same effective rate, whereby the band orientation remains substantially aligned along radial directions characteristic of the turn portion. Other a sample transport characteristics, such as electrical resistance or fluid flow resistance, of the turn portion may be adapted to reduce band broadening caused by passage of the sample through the turn portion.

52 Claims, 4 Drawing Sheets

U.S. PATENT DOCUMENTS

| | | | | |
|---|---|---|---|---|
| 5,061,361 A | | 10/1991 | Gordon | 204/299 R |
| 5,194,133 A | * | 3/1993 | Clark et al. | 204/608 |
| 5,324,413 A | | 6/1994 | Gordon | 204/299 R |
| 5,439,578 A | | 8/1995 | Dovichi | 204/299 R |
| 5,498,324 A | | 3/1996 | Yeung | 204/452 |
| 5,512,158 A | | 4/1996 | Cole | 204/453 |
| 5,730,850 A | | 3/1998 | Kambara et al. | 204/603 |
| 5,804,022 A | | 9/1998 | Kaltenbach et al. | 156/257 |
| 5,833,827 A | | 11/1998 | Anazawa et al. | 204/603 |
| 6,186,660 B1 | * | 2/2001 | Kopf-Sill | 366/340 |

OTHER PUBLICATIONS

Bartosiewicz et al., "Implementation of a capillary array electrophoresis instrument," *ISC Technical Publications, Inc.* 2/96, pp. 61–68, month unknown.

Chee et al., "Accessing Genetic Information with High–Density DNA Arrays," *Science* vol. 274, Oct. 25, 1996, pp. 610–614.

Clark et al., High–Speed Parallel Separation of DNA Restriction Fragments Using Capillary Array Electrophoresis, *Anal. Biochemistry 215*, 1993, pp. 163–170, month unknown.

Clark et al., "Multiplex dsDNA Fragment Sizing Using Dimeric Intercalation Dyes and Capillary Array Electrophoresis:Ionic Effects on the Stability and Electophoretic Mobility of DNA–Dye Complexes," *Analytical Chemistry*, vol. 69, No. 7, pp. 1355–1363, Apr. 1, 1997.

Cohen et al., "Separation and analysis of DNA sequence reaction products by capillary gel electrophoresis," *Journal of Chromatography*, 516, 1990, pp. 49–60, month unknown.

Drossman et al., "High–Speed Separations of DNA Sequencing Reactions by Capillary Electrophoresis," *Anal. Chem.* vol. 62, 1990, pp. 900–903, month unkown.

Effenhauser et al., "Glass Chips for High–Speed Capillary Electrophoresis Separations with Submicrometer Plate Heights," *Anal. Chem.*, vol. 65, 1993, pp. 2637–2642, Oct.

Effenhauser et al., "High–Speed Separation of Antisense Oligonucleotides on a Micromachined Capillary Electrophoresis Device," *Anal. Chem.* vol.66, 1994, pp. 2949–2953, Sep.

Feder et al., "A novel MHC class I–like gene is mutated in patients with hereditary haemochromatosis," *Nature genetics*, vol.13, 8/1996, pp. 399–408, month unknown.

Glazer et al., "Energy–transfer fluorescent reagents for DNA analyses," *Anal. Biotech.*, 1997, pp. 94–102.

Harrison et al., "Capillary Electrophoresis and Sample Injection Systems Integrated on a Planar Glass Chip," *Anal. Chem.*, vol. 64, 1992, pp. 1926–1932, Sep.

Harrison et al., "Micromachining a Miniaturized Capillary Electrophoresis–Based Chemical Analysis System on a Chip," *Science*, vol. 261, Aug. 13, 1993, pp. 895–897.

S. Hjerten, "High–Performance Electrophoresis Elimination of Electroendosmosis and Solute Adsorption," *Journal of chromatography*, 347, 1985, pp. 191–198, month unknown.

Huang et al., "Capillary Array Electrophoresis Using Laser–Excited Confocal Fluorescence Detection," *Anal. Chem.*vol. 64, 1992, pp. 968–972, Apr.

Huang et al., "DNA Sequencing Using Capillary Array Electrophoresis," *Anal. Chem.*, vol. 64, 1992, pp. 2149–2154, Sep.

Jacobson et al., "Microchip Capillary Elelctrophoresis with an Integrated Postcolumn Reactor," *Anal. Chem.*, vol.66, 1994, pp. 3472–3476, Oct.

Jacobson et al., "Integrated Microdevice for DNA Restriction Fragment Analysis," *Anal. Chem.*, vol. 68, 1996, pp. 720–723, month unknown.

Kheterpal et al., "DNA sequencing using a four–color confocal fluorescence capillary array scanner," *Electrophoresis*, vol.17, 1996, pp. 1852–1859, month unknown.

Kostichka et al., "High speed automated DNA sequencing in ultrathin slab gels." *Biotechnology*, vol. 10, 1/92, pp. 78–81, Jan.

Landers et al., "Capillary Electrophoresis: A Powerful Microanalytical Technique for Biologically Active Molecules," *Biotechniques*, vol.14,no.1, 1993, pp. 98–111.

Li et al., "Transport, Manipulation, and Reaction of Biological Cells On–Chip Using Electrokinetic Effects," *Anal. Chem.*, vol.69, 1997, pp. 1564–1568, Apr.

Manz et al., "Capillary electrophoresis on a chip," *Journal of Chromatography*, 593, 1992, pp. 253–258, month unknown.

Merryweather et al., "Global prevalence of putative haemochromatosis mutations," *Med Genet*, 1997, pp. 275–278, Jan.

Miller et al., "A simple salting out procedure for extracting DNA from human nucleated cells," *Nucleic Acids Research*, vol.16, No.3, 1988, p. 1215, month uknown.

Scriver, M.D. et al., "The metabolic and molecular bases of inherited disease," Chemochromatosis, chapter 69, 1995, pp. 2237–2269, month unknown.

G.F. Sensabaugh, "Commentary," *Blood Cells, Molecules, and Diseases*, 22, Aug. 31, 1996, pp. 194a–194b.

Simpson et al., "Microfabrication Technology for the Production of Capillary Array Electrophoresis Chips," Department of Chemistry, University of CA, Berkeley, pp. 15.

Simpson et al., "High–throughput genetic analysis using microfabricated 96–sample capillary array electrophoresis microplates," *Proc. Natl. Acad. Sci. USA*, vol. 95, pp. 2256–2261, 3/1998, pp. 2256–2261.

Swerdlow et al., "Capillary gel electrophoresis for rapid, high resolution DNA sequencing," *Nucleic Acids Research*, vol. 18, no.6, 1990 Oxford University Press, pp. 1415–1419, month unknown.

Takahashi et al., "Multiple Sheath–Flow Gel Capillary–Array Electrophoresis for Multicolor Fluorescent DNA Detection," *Anal. Chem.* 1994, 66, pp. 1021–1026, Apr.

Ueno et al., "Simultaneous Monitoring of DNA Fragments Separated by Electrophoresis in a Multiplexed Array of 100 Capillaries," *Anal. Chem.* 66, 1994, pp. 1424–1431, May.

Wang et al., "High–resolution capillary array electrophoretic sizing of multiplexed short tandem repeat loci using energy–transfer fluorescent primers," *Electrophoresis, 17*, 1996, pp. 1485–1490, month unknown.

Wang et al., "Microsatellite–based cancer detection using capillary array electrophoresis and energy–transfer fluorescent primers," *Electrophoresis, 18*, 1997, pp. 1742–1749, month unknown.

Woolley et al., "Ultra–high–speed DNA fragment separations using microfabricated capillary array electrophoresis chips," *Proc. Natl. Acad. Sci. USA*, vol. 91, 11/1994, pp. 11348–11352, month unknown.

Wolley et al., "Ultra–high–speed DNA sequencing using capillary electrophoresis chips," *Anal. Chem.*, 67, 1995, pp. 3676–3680, Oct.

Wolley et al., "Functional Integration of PCR Amplification and Capillary Electrophoresis in a Microfabricated DNA Analysis Device," *Anal. Chem.*, vol. 68, no.23, pp. 4081–4086, Dec.

Wolley et al., "High–speed DNA genotyping using microfabricated capillary array electrophoresis chips," *Anal. Chem.*, vol.69, no.11, pp. 2181–2186, Jun.

Schmalzing et al., "DNA Sequencing on Microfabricated Electrophoretic Devices," *Anal Chem.*, vol. 70, no. 11, Jun. 1, 1998, pp. 2303–2310, Jun.

Culbertson et al., "Disperson Sources for Compact Geometries on Microchips," *Anal. Chem.*, vol. 70, no. 18, Sep. 15, 1998, pp. 3781–3789, Sep.

Liu et al., "Optimization of High–Speed DNA Sequencing on Microfabricated Capillary Electrophoresis Channels," *Anal. Chem.*, pp. A–H, month unknown.

Seiler et al., "Planar Glass Chips for Capillar Electrophoresis: Repetitive Sample Injection, Quantitation, and Separation Efficiency," *Anal. Chem.*, vol. 65, no. 10, May 15, 1993, pp. 1481–1488.

Jacobson et al., "Effects of Injection Schemes and Column Geometry on the Performance of Microchip Electrophoresis Devices," *Anal. Chem.*, vol. 66, no. 7, Apr. 1, 1994, pp. 1107–1113.

Moore et al., "Microchip Separations of Neutral Species via Micellar Electrokinetic Capillar Chromatography," *Anal. Chem.*, vol. 67, no. 22, Nov. 15, 1995, pp. 4184–4189.

* cited by examiner

APPARATUS AND METHODS FOR HIGH RESOLUTION SEPARATION OF SAMPLE COMPONENTS ON MICROFABRICATED CHANNEL DEVICES

CROSS REFERENCE TO RELATED APPLICATIONS

This application is related to U.S. application Ser. No. 08/965,738, filed Nov. 7, 1997, and entitled "Microfabricated Capillary Array Electrophoresis Device and Method," which is incorporated herein by reference.

STATEMENT AS TO FEDERALLY SPONSORED RESEARCH

This invention was made with Government support under Grant No. FG0391ER61125, which was awarded by the U.S. Department of Energy, and Grant No. HG01399, which was awarded by the National Institutes of Health. The Government has certain rights in the invention.

BACKGROUND OF THE INVENTION

The invention relates to apparatus and methods for separating sample components, such as apparatus and methods for high resolution separation of sample components on microfabricated channel devices.

Sample component separation techniques (e.g., capillary electrophoresis) may be used in many diagnostic and gene identification procedures, such as gene mapping, polymorphism detection, gene sequencing and disease diagnosis, to separate deoxyribonucleic acid (DNA), ribonucleic acid (RNA), proteins, or other small molecular analytes according to their physical and chemical properties. In accordance with the sample component separation technique of capillary electrophoresis, molecules are transported in a capillary (or channel) which is connected to a buffer-filled reservoir. These capillaries can also be formed by microfabrication techniques on planar (typically glass) substrates. An electric field is applied between the ends of the channel to cause the molecules to migrate. Samples are typically introduced at a high potential end and, under the influence of the electric field, move toward a low potential end of the channel. After migrating through the channel, the separated sample components are detected by a suitable detector.

SUMMARY OF THE INVENTION

In one aspect, the invention features a sample component separation apparatus comprising a separation channel having at least one turn portion configured to reduce band-broadening caused by passage of a sample through the turn portion.

In another aspect, the invention features a sample component separation apparatus, comprising a separation channel having at least one substantially straight portion and at least one turn portion with a sample transport characteristic in the turn portion that is different from the corresponding sample transport characteristic of the straight portion.

Embodiments may include one or more of the following features.

The separation channel may be configured to perform an electrophoretic separation. The turn portion may have an effective channel width in the plane of the turn that is less than the effective channel width of the substantially straight portion. A tapered transition portion may be provided to couple the wider substantially straight portion of the channel to the narrower turn portion. A transition region may also be provided that has an effective channel width that increases from the narrower turn portion to the wider substantially straight portion. The increase in effective channel width of the transition portion may be substantially linear, stepped or curved. The transition portion may define a curved path.

The turn portion has an inside wall and an outside wall. The velocity of a sample component near the inside wall of the turn portion may be less than the velocity of a different component of the same sample near the outside wall of the turn portion. The turn portion may include one or more sample transport barriers. The sample transport barriers may be disposed to retard the transport of sample molecules close to the inside wall of the turn portion relative to the transport of molecules close to the outside wall of the turn portion. A plurality of sample transport barriers may be disposed in the turn portion of the separation channel with a density that is higher in regions near the inside wall than in regions near the outside wall. The sample transport barrier density preferably increases along a direction from the outside wall to the inside wall.

In yet another aspect, the invention features a method of making a sample component separation apparatus, comprising: forming a cathode reservoir in a substrate; forming, an anode reservoir in the substrate; and forming in the substrate a separation channel that defines, between the cathode reservoir and the anode reservoir, a sample transport path having a substantially straight portion and at least one turn portion with a sample transport characteristic that is different from the sample transport characteristic of the substantially straight portion of the sample transport path.

In another aspect, the invention features a method of separating a sample by electrophoresis, comprising: depositing a sample into a sample reservoir in a capillary array electrophoresis substrate; injecting a portion of the sample into a portion of a separation channel defined in the substrate; and applying a running voltage between a cathode reservoir and an anode reservoir in the substrate so as to drive the sample along the separation channel which defines in the substrate, between the cathode reservoir and the anode reservoir, a sample transport path having a substantially straight portion and at least one turn portion with a sample transport characteristic that is different from the sample transport characteristic of the substantially straight portion of the sample transport path.

Among the advantages of the invention are the following.

By reducing band-broadening caused by passage of a sample through turns in a separation channel, the invention provides a high-resolution sample component separation apparatus with a small overall footprint. For example, long separation channels, which provide high resolution separations, may be provided on a relatively small substrate. This feature is particularly advantageous for DNA sequencing, which is a technique that may require separation channel lengths of 10 cm or more. Furthermore, the invention allows the channel and reservoir layout to be optimized over a small area The invention also allows the convenient layout of multiple microfabricated capillaries on a single substrate.

The invention may be applied to all types of microfabricated separation devices, including those that perform capillary electrophoresis, free zone electrophoresis, micellar electrokinetic chromatography, conventional electrochromatography, and isoelectric focusing. Possible applications of the invention include DNA sequencing, protein separation, amino acid separation, DNA fragment sizing, PCR fragment sizing, immunoassay, SNP typing, gene expression mapping, or other analytes that have been separated by electrophoresis or capillary chromatography or capillary electrochromatography in the literature. Any device that is separation-oriented in nature will benefit from the increased channel length that the invention now permits.

Other features and advantages will become apparent from the following description, including the drawings and the claims.

BRIEF DESCRIPTION OF THE DRAWINGS

FIGS. 6A–6C are diagrammatic top views of a separation channel that has a straight portion and a turn portion with an effective channel width that is less than the effective channel widths of the straight portions, shown at different times during a sample component separation run.

DESCRIPTION OF THE PREFERRED EMBODIMENTS

Figures 1, 2:
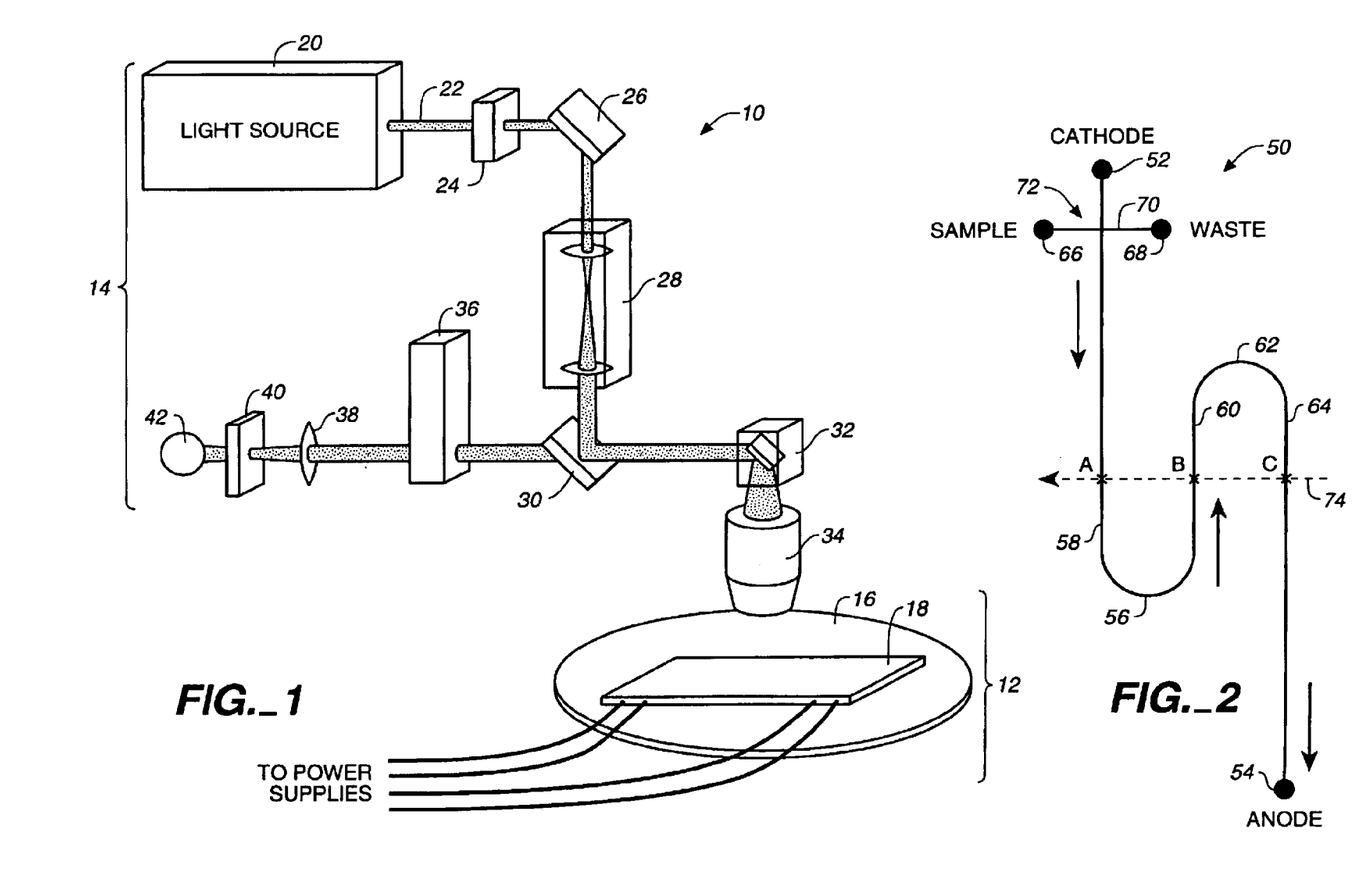
FIG. 1 is a diagrammatic perspective view of a sample component separation apparatus.
FIG. 2 is a diagrammatic top view of a channel and reservoir layout for a sample component separation apparatus with two turns and three straight sections.

Referring to FIG. 1, as described in Simpson et al., "High-Throughput Genetic Analysis Using Microfabricated 96-sample Capillary Array Electrophoresis Microplates," Proc. Natl. Acad. Sci., USA, vol. 95, ¶. 2256–2261 (March 1998), which is incorporated herein by reference, a sample component separation apparatus 10 (e.g., a capillary electrophoresis device) includes a separation system 12 and a detection system 14. Separation system 12 includes a substrate 16 with one or more separation channels and an electrode system 18 for biasing the one or more separation channels. One embodiment of detection system 14 includes a light source 20 (e.g., a continuous-wave argon ion laser operating at a wavelength of 488 nm, or a frequency-doubled Nd:YAG laser operating at a frequency of 532 nm) for producing a light beam 22 which is selected to induce fluorescent emission in samples migrating through separation system 12. Light beam 22 passes through an excitation filter 24 to a mirror 26, which directs light beam 22 to a beam expander 28. A dichloric beam splitter 30 directs light beam 22 to a galvo-scanner 32 which scans the beam across the aperture of a confocal lens assembly 34. The beam is focused onto separation system 12 with a spot size of, e.g., about 5 microns, and scanned across the separation channels of separation system 12. Fluorescent light emitted from the samples migrating through separation system 12 are collected by confocal lens assembly 34 and directed to dichloric beam splitter 30, which is substantially transparent to the wavelengths of the collected fluorescent light. An emission filter 36, which operates, e.g., in the range of about 545–620 nm, directs the collected fluorescent light to a lens 38 that focuses the fluorescent light through a pinhole aperture 40 before the light is detected by a detector 42 (e.g., a photo-multiplier tube).

Referring to FIG. 2, in one embodiment, separation system 12 includes a separation channel 50 that is coupled between a cathode reservoir 52 and an anode reservoir 54. Separation channel 50 has a first turn portion 56, which is coupled between straight portions 58, 60, and a second turn portion 62, which is coupled between straight portions 60, 64. A sample reservoir 66 and a waste reservoir 68 are coupled to separation channel 50 by an injection channel 70, which intersects separation channel 50 at an intersection 72. In operation, electrode system 18 applies an injection voltage (e.g., 300 volts) across sample reservoir 66 and waste reservoir 68. During this time electrode system 18 applies a biasing voltage (e.g., 100 volts) across cathode reservoir 52 and anode reservoir 54 to reduce diffusion of the sample into separation channel 50. After fluid from sample reservoir 66 reaches intersection 72, electrode system 18 applies a separation voltage (e.g., 1,000 volts) between cathode reservoir 52 and anode reservoir 54 to draw a sample into separation channel 50. After a suitably sized (e.g, 100 microns in length) sample (injection plug) has been drawn into separation channel 50, electrode system 18 applies a back-bias voltage (e.g., 200 volts) across sample reservoir 66 and waste reservoir 68 to clear excess sample from intersection 72. In this embodiment, detection system 14 may scan light beam 22 across separation channel 50 along a scan line 74 that intersects separation channel 50 at three locations (A, B, and C) along the sample transport path.

Figure 3A:
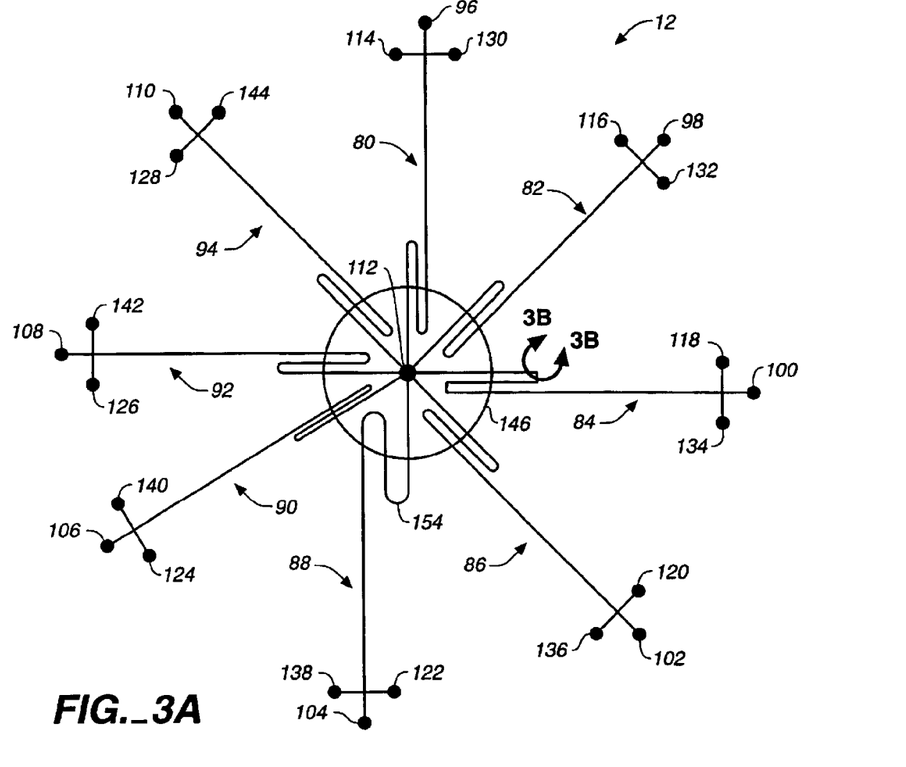
FIG. 3A is a diagrammatic top view of a channel and reservoir layout for another sample component separation apparatus with differing turn geometries.

Referring to FIG. 3A, in another embodiment, separation system 12 includes a plurality of separation channels 80–94 that are coupled between respective cathode reservoirs 96–110 and a common anode reservoir 112. Each separation channel 80–94 includes first and second turn portions coupled between straight portions. Separation channel 84 includes abrupt 90° turn portions, whereas each of the other separation channels 80, 82, and 86–94 includes curved turn portions. Also note that the radius of curvature of the turn portions of separation channel 88 is larger than the radii of curvature of the turn portions of the other separation channels, and that the radius of curvature of the turn portions of separation channel 90 is smaller than the radii of curvature of the turn portions of the other separation channels. Each separation channel 80–94 is coupled to a respective sample reservoir 114–128 and a respective waste reservoir 130–144. Samples may be injected into separation channels 80–94 using the biasing technique described above in connection with the embodiment of FIG. 2. In this embodiment, a rotary confocal detection system described in U.S. Ser. No. 09/015,198, filed Jan. 29, 1998, and entitled "Rotary Confocal Scanner for Detection of Capillary Arrays," which is incorporated herein by reference, may scan light beam 22 along a circular scan path 146 (e.g., with a radius of about 1 cm, and at a scan rate of about 10 Hz) centered at anode reservoir 112. Because scan path 146 traverses each separation channel 80–94 at three different locations, detection system 14 may collect three data points from each channel during each scan cycle.

In the embodiments described above, samples are transported along separation channels as a result of a separation voltage applied by electrode system 18. As the samples migrate along the separation channels, components of the samples become physically separated based on differences in their physical and chemical properties. The amount of separation and, consequently, the resolution of the apparatus, increases with the distance that the sample travels along the separation channel. Turn portions are used to increase the sample transport path, while maintaining a relatively small overall footprint for the separation system 12. The use of turn portions also provides flexibility in optimizing the layout of the separation channel and the various reservoirs. As explained in detail below, the turn portions are configured to reduce band broadening caused by passage of a sample through these turn portions.

Figure 3B:
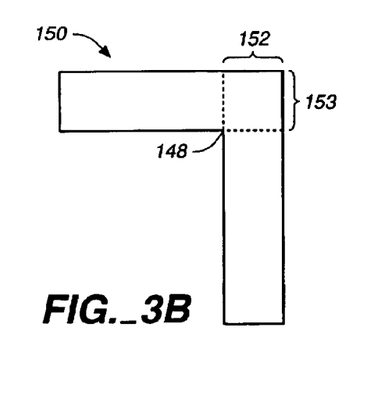
FIG. 3B is a diagrammatic top view of a turn portion of the indicated separation channel of the embodiment of FIG. 3A FIGS. 4A–4C are diagrammatic top views of a separation channel that has straight portions and a turn portion with substantially the same effective channel widths, shown at different times during a sample component separation run.

As used herein, the term "turn portion" refers generally to a portion of a separation channel that defines a sample transport path along a direction that is different than the direction from which the sample was traveling through a "straight portion" just before the sample entered the separation channel portion in question. A turn portion may define an overall sample transport path that corresponds to a change in direction of x°, where 0°<x<360°. The sample transport path defined by a turn portion may correspond to an abrupt change in direction (e.g., the 90° turn portions of separation channel 84) or, alternatively, may correspond to a gradual change in direction (e.g., the 180° turn portions of separation channels 80, 82, and 86–90). Each turn portion is characterized by an inside wall and an outside wall, where the sample transport path along the outside wall is greater than the sample transport path along the inside wall, as measured between locations that lie along lines that are orthogonal to the inside and outside walls at the ends of the turn portion. For example, as shown in FIG. 3B, an inside wall 148 of a 90° turn portion of separation channel 84 has an infinitesimally short length, whereas the corresponding outside wall 150 has a length equal to the lengths of segments 152 and 153. Similarly, for the 180° turn portion 154 of separation channel 88, the inside wall, which is closer to anode 112, corresponds to a sample transport path that is shorter than the sample transport path corresponding to the outside wall, which is closer to cathode 104. Other turn portions are possible. For example, referring to FIG. 7D (discussed below), turn portions 229 and 230 may have curved inner and outer walls that together define a curved sample transport path. Alternatively, as shown in FIG. 7E (discussed below), turn portion 231 may have a substantially straight inner wall 233 and a curved outer wall 235, wherein the direction of sample transport path defined along outer wall 235 is different than the direction from which the sample was traveling through straight portion 237. Thus, the sample transport path defined along outer wall 235 is greater than the sample transport path defined along inner wall 233.

As mentioned above and described in detail below, the separation channel turn portions are configured to reduce band-broadening caused by passage of a sample through the turn portion. The band-broadening results, at least in part, from the difference in separation paths defined along the inside and outside walls of the turn portion. Assuming the molecules of a sample band travel through a turn portion at the same velocity, the molecules near the inside wall of the turn portion will complete the turn more quickly than the molecules near the outside wall. There are also electric field inhomogeneities that result from the difference in turn lengths traversed by the molecules of a sample band. The velocity (v) of a band is the product of its mobility ($\mu$E), which is substantially constant for a given band, and the magnitude of the electric field (E) inside the turn portion:

$$V = \mu_E E \quad (1)$$

The electric field strength gradient perpendicular to the axis of the turn portion also contributes to the band-broadening effect because the electric field is greater near the inside wall than near the outside wall. Thus, the molecules near the inside wall not only have a shorter distance to travel through the turn portion, but they also move more quickly through the turn portion. In addition, for capillary electrochromatography or other chromatography-based separation techniques, where fluid flow is induced in the channel, the path along the inside wall of the turn portion has a lower flow resistance than the path along the outside wall.

Figure 4A:
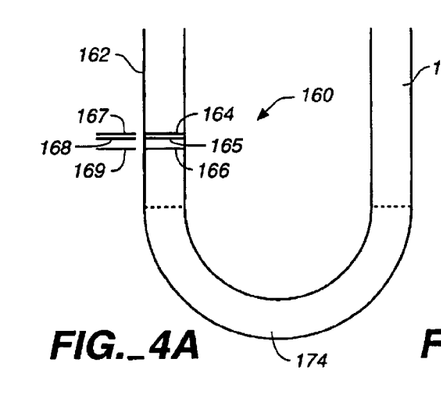
Figures 4B, 6B:
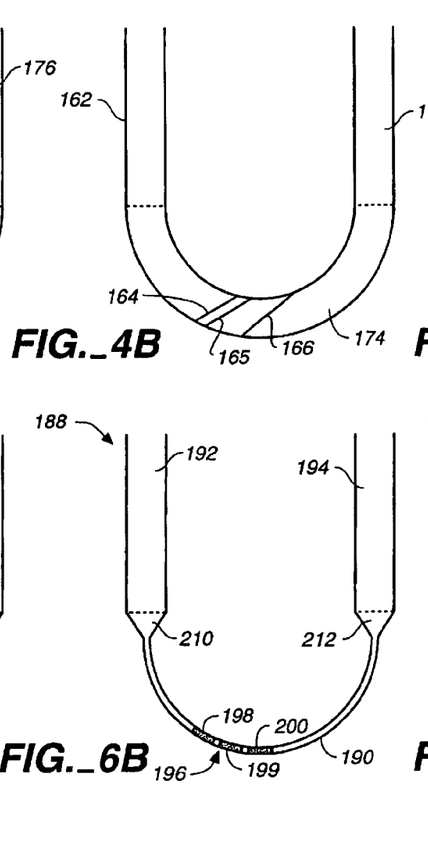
Figures 4C, 6C:
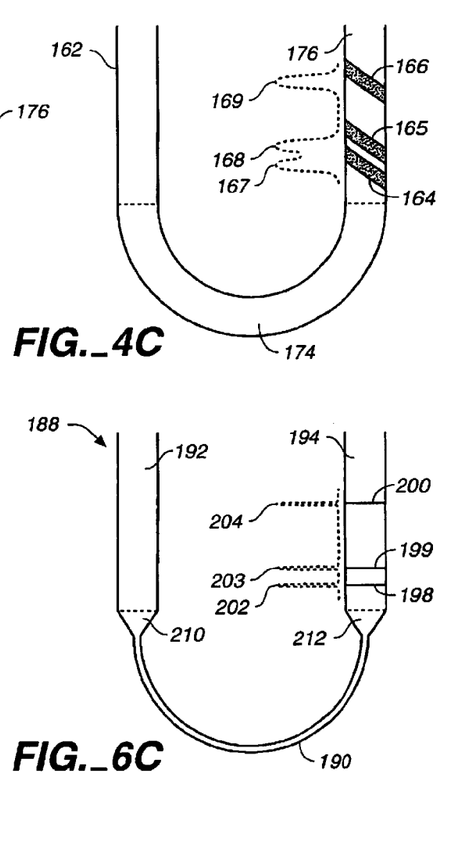

As shown in FIGS. 4A–4C, the net result of these factors is that the sample bands emerge from a turn portion with a tilted orientation that appears to detection system 14 as a broadened band, especially after lateral diffusion. As an injection plug 160 migrates through a straight portion 162 of a separation channel, the constituent molecules of injection plug 160 separate into bands 164–166, which are detected by detection system 14 overtime as three distinct fluorescence peaks 167–169 (FIG. 4A). As bands 164–166 travel through straight portion 162, they remain substantially orthogonal to the walls of the separation channel. Referring to FIG. 4B, for the reasons explained above, bands 164–166 become tilted with respect to radial directions characteristic of turn portion 174 (i.e., each band intersects the walls of the turn portion at acute angles rather than at right angles). When bands 164–166 emerge from turn portion 174 and enter a straight portion 176 (FIG. 4C), they are significantly tilted. After diffusion across the channel occurs the peaks 167–169 are broadened and merged, thereby decreasing the resolution of sample component separation apparatus 10.

Figure 5:
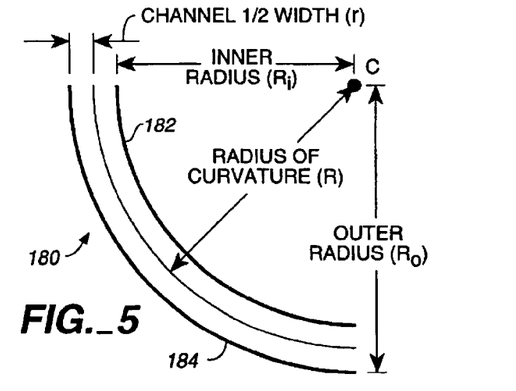
FIG. 5 is a diagrammatic top view of part of a turn portion of a separation channel.

Referring to FIG. 5, the change in band width resulting from passage of a band through a turn portion may be described in terms of several parameters that may characterize a given turn portion. For the purpose of the following discussion, a circular turn portion 180 has a characteristic channel width (2r), a characteristic radius of curvature (R), an inside wall 182 with a characteristic radius ($R_i$), and an outside wall 184 with a characteristic radius ($R_O$). The lengths of the sample transport path along the inside wall ($L_{inside}$) and the outside wall ($L_{outside}$) are given by:

$$L_{inside} = \theta(R_i) = \theta(R-r) \quad (2)$$

$$L_{outside} = \theta(R_o) = \theta(R+r) \quad (3)$$

where $\theta$ is the angle of the turn portion expressed in radians. Based on Equation (1) and the fact that the magnitude of the electric field (E) is given by the quotient of the applied voltage (V) and the sample path length (L), the sample band velocities along inside wall 182 ($v_{inside}$) and along outside wall 184 ($V_{outside}$) are, in the simplest interpretation, given by:

$$v_{inside} = \frac{\mu_E V}{L_{inside}} \quad (4)$$

$$v_{outside} = \frac{\mu_E V}{L_{outside}} \quad (5)$$

The length of time needed for a sample band to travel through turn portion 180 is given by the quotient of the path length and the band velocity. Thus, based on Equations (4) and (5), the time needed to traverse a path along inside wall 182 ($t_{inside}$) and the time needed to traverse a path along the outside wall ($t_{outside}$) are given by:

$$t_{inside} = \frac{L_{inside}}{v_{inside}} = \frac{\theta^2 (R-r)^2}{\mu_E V} \qquad (6)$$

$$t_{outside} = \frac{L_{outside}}{v_{outside}} = \frac{\theta^2 (R+r)^2}{\mu_E V} \qquad (7)$$

Based on Equations (6) and (7), the difference in time (Δt) for the sample band to traverse inside wall 182 and outside wall 184 is given by:

$$\Delta t = t_{outside} - t_{inside} = \frac{\theta^2 4Rr}{\mu_E V} \qquad (8)$$

Finally, the change in band width (Δw) caused by passage of the sample through the turn is given by the product of Δt (given by Equation (8)) and the average velocity of the band ($v_{average}$), which is assumed to correspond to the band components traveling along a path through the center of turn portion 180:

$$\Delta w = v_{average} \Delta t = \frac{\mu_E V}{\theta R} \cdot \frac{\theta^2 4Rr}{\mu_E V} = 4\theta r \qquad (9)$$

Thus, for a given turn angle θ, the band broadening resulting from passage of a sample through a turn portion may be reduced by decreasing the effective channel width (2r) through the turn portion.

Thus, to reduce band broadening caused by passage of a sample through a turn portion, the turn portion may be constructed and arranged to have a sample transport characteristic that is different from the corresponding sample transport characteristic of the straight portion. For example, the turn portion may be configured with an effective channel width that is smaller than the effective channel widths of the straight portions of the separation channel. The actual channel width of the turn portion may be smaller than the channel widths of the straight portions; the effective channel width of the turn portion may be reduced by placing one or more sample transport barriers in the turn portion of the channel. Alternatively, the sample migration through the turn portion may be controlled so as to reduce band broadening. For example, sample transport barriers may be configured so that sample components of a given band travel through the turn portion at substantially the same rate, whereby the band orientation remains substantially aligned along radial directions characteristic of the turn portion. Other sample transport characteristics of the turn portion may be adapted to reduce band broadening caused by passage of the sample through the turn portion.

The band broadening induced by a turn also may be reduced if a second turn of opposite direction is introduced immediately after the first turn, as shown in the embodiment of FIG. 2. The utility of this configuration, however, depends on the diffusion constant of the analyte and the size of the band. In particular, if the initial band is very large relative to the turn volume, this configuration is likely to show little band broadening. If the band volume is small relative to the turn volume and the lateral diffusion is significant during passage through the intermediate straight section between the turns, the second turn will not significantly reduce the band broadening effect. On the other hand, if the band volume is small relative to the turn volume and the lateral diffusion is insignificant during passage through the intermediate straight section between the turns, the second turn will tend to reduce band broadening induced by the first turn.

Figure 6A:
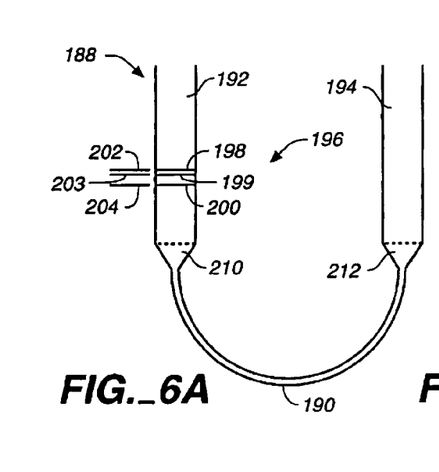

As shown in FIGS. 6A–6C, this novel approach may be implemented by providing a separation channel 188 with a turn portion 190 that has a channel width that is smaller than the width of straight portions 192, 194. As an injection plug 196 migrates through a straight portion 192 of separation channel 188, the constituent molecules of injection plug 196 separate into bands 198–200, which are detected by detection system 14 over time as three distinct fluorescence peaks 202–204 (FIG. 6A). As bands 198–200 travel through straight portion 192, their orientations remain substantially orthogonal to the walls of the separation channel. Referring to FIG. 6B, although bands 198–200 become slightly tilted with respect to the inside wall and the outside wall of turn portion 190 (i.e., each band intersects the walls of the turn portion at an acute angle), the degree of tilt is significantly less than the degree of tilt caused by passage through turn portion 174 (FIGS. 4A–4C), which has a wider channel width. When bands 198–200 emerge from turn portion 190 and enter a straight portion 194 (FIG. 6C), they are not tilted significantly. The result is that fluorescence peaks 202–204 detected by detection system 14 are only slightly broadened. In fact, the resolution of peaks 202–204 is greater than the resolution before bands 198–200 entered turn portion 190 because of the added migration distance traversed by the bands through the turn portion and because the new turn design has not degraded the resolution. Thus, the use of narrow channel width turn portions results in a sample component separation apparatus 10 with an improved resolution.

In the embodiment of FIGS. 6A–6C, the straight portions 192, 194 may have a channel width of about 138 microns (prior to tapered portions 210, 212), and turn portion 190 may have a channel width of about 33 microns (after tapered portions 210, 212). Tapered portions 210, 212 may have a length of about 200 microns.

Another advantage of narrow channel width turn portions relates to a band stacking effect. Upon entering a narrowed turn, the bands and distances between bands will increase in length. As a band travels along a turn portion, the band will experience some broadening by sample diffusion. Upon exiting the turn portion, however, the band will be reduced to its original width, and broadening caused by passage of the band through the turn portion also will be reduced. For the purpose of this discussion, the subscript "s" refers to the parameters of an injection plug in a straight portion of a separation channel, and the subscript "T" refers to the parameters of the injection plug in the turn portion. The volume of the plug in the straight portion is the same as the volume of the plug in the turn portion. Consequently:

$$w_s l_s h = w_t l_t h \qquad (10)$$

The height (h) of the separation channel is assumed to be same in the straight portion and in the turn portion, although this is not a limiting assumption that is necessary for this invention. Assuming the width ($w_t$) of the turn portion is reduced to a fraction (δ; 0<δ<1) of the width ($w_s$) of the straight portion (i.e., $w_t = \delta w_s$), the length of the plug will increase proportionally:

$$l_t = \frac{1}{\delta} \cdot l_s \qquad (11)$$

As the plug travels through the turn portion, it is also lengthened (Δl) as a result of the broadening effects discussed above that occur during passage through the turn.

Thus, the overall length ($l_{total}$) of the plug in the turn is given by:

$$l_{total} = l_t + \Delta l = \frac{1}{\delta} \cdot l_s + \Delta l \tag{12}$$

After traversing the turn portion, the plug may enter another straight portion with a channel width $w_s$. Because the plug volume is conserved, the length of the plug is decreased by the same fraction ($\delta$). Thus, the plug length ($l_{s'}$) in the second straight portion is given by:

$$l_{s'} = \delta(l_t + \Delta l) = \delta\left(\frac{1}{\delta} \cdot l_s + \Delta l\right) = l_s + \delta\Delta l \tag{13}$$

The additional lengthening ($\Delta l$) caused by passage of the plug through the turn portion is therefore reduced by the same fraction ($\delta$) that the channel width of the turn portion is reduced relative to the channel width of the straight portions of the separation channel. That is, in this way, the use of narrow width turn portions further reduces the band broadening caused by passage of the sample through the turn portion.

Figure 7A:
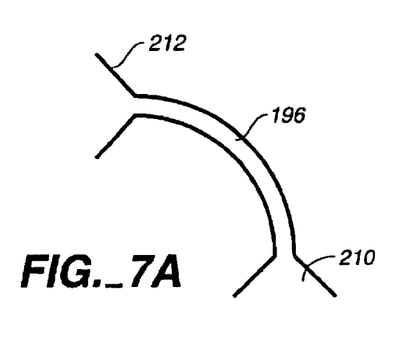
FIGS. 7A–7F are diagrammatic top views of different separation channel turn portions.

Referring back to FIGS. 6A–6C and to FIG. 7A, turn portion 196 is coupled to straight portions 192, 194 by transition portions 210, 212, which are characterized by a linear reduction in channel width from the straight portion to the turn portion of the separation channel. In this design, the channel width is reduced before the turn is entered and the channel is widened following the turn. This modification is accomplished by tapering the channel gradually in a funnel-shaped fashion rather than changing the width abruptly.

Figure 7B:
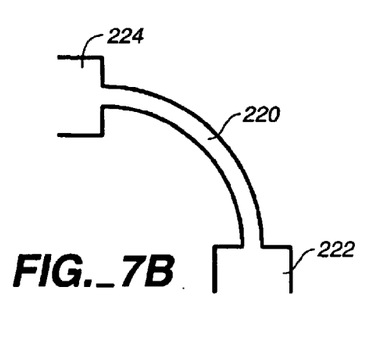
Figure 7C:
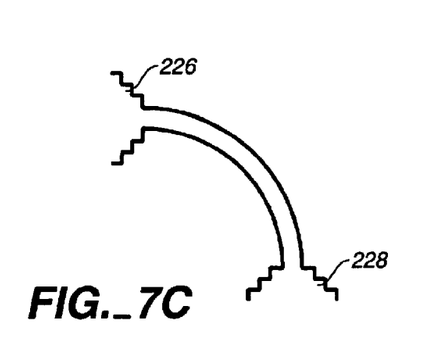
Figure 7D:
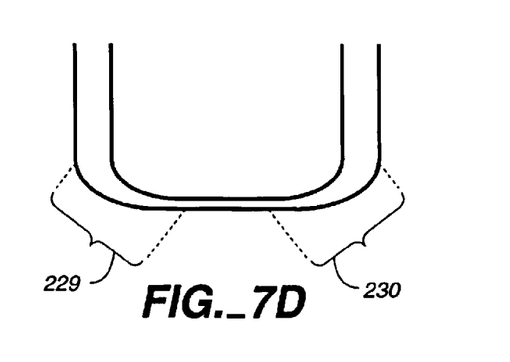
Figure 7E:
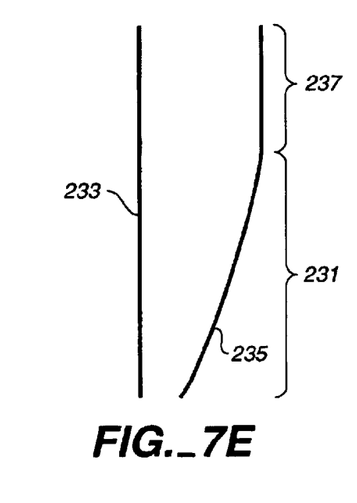

As shown in FIGS. 7B–7D, other transitions from the turn portion to the straight portions are also possible. The embodiment of FIG. 7B employs an abrupt transition between a turn portion 220 and straight portions 222, 224 (i.e., there is no transition portion). It is noted that the distortion in the sample migration pattern caused by the abrupt transition in this embodiment might induce eddies or other resolution reducing features. Referring to FIG. 7C, in another embodiment, the transition portions 226, 228 are substantially stepped. As shown in FIG. 7D, transition portions 229, 230 may be curved and have inner and outer walls that define curved paths that form the turn portions. Referring to FIG. 7E, in an alternative embodiment a turn portion 231 may be formed from a substantially straight inner wall 233 and a curved outer wall 235. The width of turn portion 231 is narrowed to reduce band-broadening caused by passage of a sample through turn portion 231.

Figure 7F:
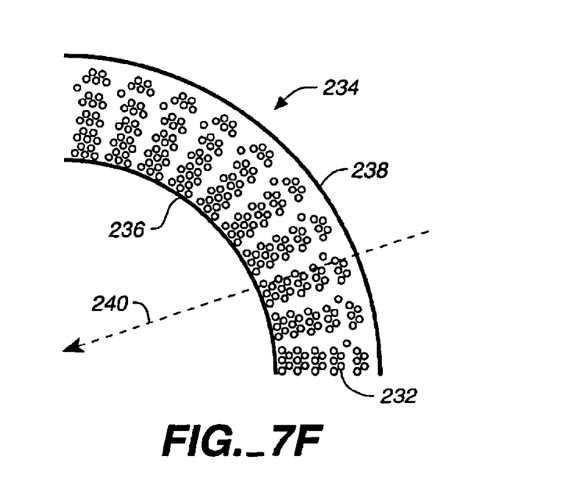

Referring to FIG. 7F, in yet another embodiment, an array of posts 232 (sample transport barriers) are placed in a turn portion 234 such that the sample velocity near inside wall embodiment a turn 236 is less than the sample velocity near outside wall 238. As shown, the sample transport barrier density increases along a radial direction 240 from outside wall 238 to inside wall 236. Posts 232 can be placed inside turn portion 234 so as to compensate for radius-dependent differences in total path length and electric field strength. For example, posts 232 may be placed so that a sample band traversing turn portion 234 remains oriented with respect to outside wall 238 and inside wall 236 along radial directions characteristic of turn portion 238, with the result that the sample band emerges from turn portion 234 with an orientation that is substantially orthogonal to the straight portion coupled to the end of turn portion 234. In effect, posts 232 reduce the mobility of the sample along inside wall 236 so that band components travel along inside wall 236 at substantially the same radial velocity as band components traveling along outside wall 238. In the case of electrophoresis, the idea is to set up posts so that the path length and resistance for small and long radius paths around the turn are the same. In the case of chromatography, the idea is to keep the fluid flow resistance for small and long radius paths the same.

The separation channels described above may be formed in substrate 16 in accordance with the fabrication methods described in U.S. application Ser. No. 08/965,738, filed Nov. 7, 1997, which has been incorporated herein by reference. For example, in one embodiment, a 3 ⅞ inch diameter, 1 mm thick mashed borofloat glass plate may be chemically etched with 49% HF for two minutes to produce separation channels with a depth of 14 microns. Patterning for wet etching was accomplished using standard photolithographic techniques. A second top plate is then bonded to the etched plate to form the channels. Holes are formed in the top plate to provide fluid access. These devices can equivalently be fabricated or molded in plastic or other polymeric structures suitable for electrophoresis of samples. These devices could also be formed from silicon wafers or other materials used in semiconductor fabrication, followed by suitable dielectric or polymeric coatings or treatment of the surfaces to make them suitable for electrophoresis.

Other embodiments are within the scope of the claims.

For example, the novel turn approach described herein may be applied to any of the capillary array electrophoresis (CAE) embodiments described in U.S. application Ser. No. 08/965,738.

What is claimed is:

1. A sample component separation apparatus, comprising a separation channel having at least one substantially straight portion and at least one turn portion configured to have a volume per unit length less than that of the straight portion to increase the length of a sample band passing through the turn portion to reduce band-broadening caused by passage of the sample band through the turn portion.

2. The apparatus of claim 1, wherein the separation channel is configured to perform an electrophoretic separation.

3. The apparatus of claim 1, wherein the turn portion has an effective channel width in the plane of the turn that is less than the effective channel width of the substantially straight portion.

4. The apparatus of claim 3, wherein the turn portion includes one or more sample transport barriers.

5. The apparatus of claim 3, further comprising a transition portion coupling the substantially straight portion and the turn portion, the transition portion having an effective channel width that increases from the narrower turn portion to the wider straight portion.

6. The apparatus of claim 5, wherein the apparatus is microfabricated and the increase in effective channel width of the transition portion is substantially linear.

7. The apparatus of claim 5, wherein the apparatus is microfabricated and the increase in effective channel width of the transition portions is stepped.

8. The apparatus of claim 5, wherein the transition portion defines a curved path.

9. A sample component separation apparatus, comprising a separation channel having at least one substantially straight portion and at least one turn portion with a volume per unit length that is less than the volume per unit length of the substantially straight portion to reduce band-broadening caused by the passage of a sample band through the turn portion.

10. A The apparatus of claim 9, wherein the separation channel is configured to perform an electrophoretic separation.

11. The apparatus of claim 9, wherein the turn portion includes one or more sample transport barriers.

12. The apparatus of claim 9, further comprising a transition portion coupling the substantially straight portion and the turn portion, the transition portion having an effective channel width that increases from the narrower turn portion to the wider straight portion.

13. The apparatus of claim 12, wherein the apparatus is microfabricated and the increase in effective channel width of the transition portion is substantially linear.

14. The apparatus of claim 12, wherein the apparatus is microfabricated and the increase in effective channel width of the transition portions is stepped.

15. The apparatus of claim 12, wherein the transition portion defines a curved path.

16. The apparatus of claim 9, wherein the turn portion has an inside wall and an outside wall, and further comprising a plurality of sample transport barriers disposed in the turn portion of the separation channel with a density that is higher in regions near the inside wall than in regions near the outside wall.

17. The apparatus of claim 16, wherein the sample transport barrier density increases along a direction from the outside wall to the inside wall.

18. A sample component separation apparatus comprising a separation channel having at least one substantially straight portion and at least one turn portion, wherein the turn portion has an inside wall and an outside wall, and wherein a plurality of sample transport barriers are disposed in the turn portion near the inside wall of the turn portion so the velocity of a sample component near the inside wall of the turn portion is less than the velocity of a different component of the same sample near the outside wall of the turn portion.

19. A sample component separation apparatus, comprising:
  a cathode reservoir;
  an anode reservoir; and
  a separation channel that defines, between the cathode reservoir and the anode reservoir, a sample transport path having at least one substantially straight portion and at least one turn portion configured to have a volume per unit length less than that of the volume per unit length of the straight portion to increase the length of a sample band passing through the turn portion.

20. The apparatus of claim 19, wherein the separation channel is configured to perform an electrophoretic separation.

21. The apparatus of claims 19, wherein the turn portion has an effective channel width that is less than the effective width of the straight portion.

22. The apparatus of claim 21, further comprising a transition portion coupling the straight portion and the turn portion, the transition portion having an effective channel width that increases from the narrower turn portion to the wider straight portion.

23. The apparatus of claims 22, wherein the apparatus is microfabricated and the increase in effective channel width of the transition portion is substantially linear.

24. The apparatus of claim 22, wherein the apparatus is microfabricated and the increase in effective channel width of the transition portion is stepped.

25. The apparatus of claim 22, wherein the transition portion is designed to reduce dispersion of sample components.

26. The apparatus of claims 19, wherein the turn portion has an inside wall and an outside wall, and the turn portion includes one or more sample transport barriers disposed to retard the transport of sample molecules close to the inside wall of the turn portion relative to the transport of molecules close to the outside wall of the turn portion.

27. The apparatus of claim 19, further comprising a plurality of separation channels, each defining, between an associated cathode reservoir and the anode reservoir, a sample transport path having at least one turn portion.

28. A sample component separation apparatus, comprising:
  cathode reservoir means;
  anode reservoir means;
  separation channel having turn portion means having a volume per unit length that is less than the volume per unit length of a substantially straight portion means of the separation channel for reducing band-broadening caused by passage of an electrophoretic sample through the turn portion means;
  sample reservoir means coupled to the separation channel; and
  waste reservoir means coupled to the separation channel.

29. A method of separating a sample by electrophoresis, comprising:
  depositing a sample into a sample reservoir in a capillary electrophoresis substrate;
  injecting a portion of the sample into a portion of a separation channel; and
  applying a voltage between a cathode reservoir and an anode reservoir in the substrate so as to drive the sample along the separation channel which defines in the substrate, between the cathode reservoir and the anode reservoir, a sample transport path having a substantially straight portion and at least one turn portion configured to have a volume per unit length less than that of the volume per unit length in the straight portion to increase the length of a sample band passing through the turn portion to reduce band-broadening caused by passage of the sample band through the turn portion.

30. The method of claim 29, wherein the separation channel is configured to perform an electrophoretic separation.

31. The method of claim 29, wherein the turn portion includes one or more sample transport barriers.

32. The method of claim 29, wherein the turn portion has an effective channel width in the plane of the turn that is less than the effective channel width of the substantially straight portion.

33. The method of claim 32, wherein the turn portion includes one or more sample transport barriers.

34. The method of claim 32, further comprising a transition portion coupling the substantially straight portion and the turn portion, the transition portion having an effective channel width that increases from the narrower turn portion to the wider straight portion.

35. The method of claim 34, wherein the increase in effective channel width of the transition portion is substantially linear.

36. The method of claim 34, wherein the increase in effective channel width of the transition portions is stepped.

37. The method of claim 34, wherein the transition portion defines a curved path.

38. The method of claim 29, wherein the turn portion has an inside wall and an outside wall, and the velocity of a sample component near the inside wall of the turn portion is less than the velocity of a different component of the same sample near the outside wall of the turn portion.

39. The method of claim 29, wherein the turn portion has an inside wall and an outside wall, and further comprising a plurality of sample transport barriers disposed in the turn portion of the separation channel with a density that is higher in regions near the inside wall than in regions near the outside wall.

40. The method of claim 39, wherein the sample transport barrier density increases along a direction from the outside wall to the inside wall.

41. The apparatus of claim 1, 19 or 29 wherein at least one of the effective channel width and depth of the turn portion is less that than of the straight portion.

42. A method of separating a sample by electrophoresis, comprising:
  depositing a sample into a sample reservoir in a capillary electrophoresis substrate;
  injecting a portion of the sample into a portion of a separation channel; and
  applying a voltage between a cathode reservoir and an anode reservoir in the substrate so as to drive the sample along the separation channel which defines in the substrate, between the cathode reservoir and the anode reservoir, a sample transport path having a substantially straight portion and at least one turn portion having an inside wall and an outside wall, and the turn portion including one or more sample transport barriers disposed to retard the transport of sample molecules close to the inside wall of the turn portion relative to the transport of molecules close to the outside wall of the turn portion.

43. The method of claim 29 or 42, further comprising a plurality of separation channels, each defining, between an associated cathode reservoir and the anode reservoir, a sample transport path having at least one turn portion.

44. A sample component separation apparatus, comprising a separation channel having at least one turn portion including one or more sample transport barriers to reduce band-broadening caused by passage of a sample through the turn portion.

45. The apparatus of claim 44, wherein the turn portion has an inside wall and an outside wall, and a plurality of the sample transport barriers are disposed in the turn portion of the separation channel with a density that is higher in regions near the inside wall than in regions near the outside wall.

46. The method of claim 43, wherein the sample transport barrier density increases along a direction from the outside wall to the inside wall.

47. A sample component separation apparatus, comprising a separation channel having at least one substantially straight portion and at least one turn portion configured to have a volume that is less than that of a sample plug in the straight portion to increase the length of the sample plug passing through the turn portion to reduce band-broadening caused by passage of the sample plug through the turn portion.

48. The apparatus of claim 47, wherein the separation channel is configured to perform an electrophoretic separation.

49. The apparatus of claim 47, further comprising a transition portion coupling the substantially straight portion and the turn portion, the transition portion having an effective channel width that increases from the turn portion to the straight portion.

50. The apparatus of claim 49, wherein the apparatus is microfabricated and the increase in effective channel width of the transition portion is substantially linear.

51. The apparatus of claim 49, wherein the apparatus is microfabricated and the increase in effective channel width of teh transition portion is stepped.

52. The apparatus of claim 49, wherein the transition portion defines a curved path.

* * * * *

UNITED STATES PATENT AND TRADEMARK OFFICE
CERTIFICATE OF CORRECTION

PATENT NO. : 6,913,679 B1
DATED : July 5, 2005
INVENTOR(S) : Mathies et al.

It is certified that error appears in the above-identified patent and that said Letters Patent is hereby corrected as shown below:

Column 10,
Line 58, "portions is" should be -- portion is --.

Column 11,
Line 1, "A The apparatus" should be -- The apparatus --.
Line 59, "claims 22" should be -- claim 22 --.

Column 12,
Line 1, "claims 19" should be -- claim 19 --.
Line 15, "channel having" should be -- channel means having --.
Line 67, "the velocity" should be -- the radial velocity --.

Column 13,
Line 2, "less than the velocity" should be -- substantially the same as the radial velocity --.
Line 15, "less that than" should be -- less than that --.

Column 14,
Line 34, "teh transition" should be -- the transition --.

Signed and Sealed this

Eighteenth Day of October, 2005

JON W. DUDAS
*Director of the United States Patent and Trademark Office*